United States Patent
Collins

(10) Patent No.: US 6,231,596 B1
(45) Date of Patent: May 15, 2001

(54) SURGICAL INSTRUMENT WARMING DEVICE

(75) Inventor: L. Dale Collins, Eufaula, OK (US)

(73) Assignee: Heat Max, Inc., Dalton, GA (US)

( * ) Notice: Subject to any disclaimer, the term of this patent is extended or adjusted under 35 U.S.C. 154(b) by 0 days.

(21) Appl. No.: 09/137,715

(22) Filed: Aug. 21, 1998

Related U.S. Application Data

(60) Provisional application No. 60/094,371, filed on Jul. 27, 1998.

(51) Int. Cl.[7] ............................................. A61F 7/00
(52) U.S. Cl. .................. 607/114; 607/112; 126/263.02; 126/263.07
(58) Field of Search ..................... 607/112, 114; 126/229, 263.01, 263.02, 226, 263.07; 2/161.7; 602/14; 606/24

(56) References Cited

U.S. PATENT DOCUMENTS

| | | | |
|---|---|---|---|
| Re. 32,026 | 11/1985 | Yamashita et al. | 126/263 |
| 1,953,513 | 4/1934 | Simmons | 150/1 |
| 3,951,127 * | 4/1976 | Watson et al. | 126/206 |
| 4,049,408 * | 9/1977 | Patel | 62/4 |
| 4,106,478 | 8/1978 | Higashijima | 126/263 |
| 4,516,564 | 5/1985 | Koiso et al. | 126/263 |
| 4,756,299 * | 7/1988 | Podella | 126/263 |
| 4,834,654 * | 5/1989 | Nussbaum | 433/141 |
| 4,934,336 * | 6/1990 | White | 126/263 |
| 4,981,135 * | 1/1991 | Hardy | 128/402 |
| 5,020,509 | 6/1991 | Suzuki et al. | 126/263 |
| 5,020,711 * | 6/1991 | Kelley | 224/222 |
| 5,046,479 | 9/1991 | Usui | 126/204 |
| 5,304,216 * | 4/1994 | Wallace | 607/112 |
| 5,366,492 * | 11/1994 | Ueki | 607/114 |
| 5,378,531 * | 1/1995 | Larson et al. | 428/255 |
| 5,676,642 * | 10/1997 | Peters | 602/27 |
| 5,800,492 * | 9/1998 | Manker | 607/111 |
| 5,837,005 * | 11/1998 | Viltro et al. | 607/112 |
| 5,891,187 * | 4/1999 | Winthrop et al. | 607/96 |
| 5,968,072 * | 10/1999 | Hite et al. | 606/202 |

* cited by examiner

Primary Examiner—Linda C. M. Dvorak
Assistant Examiner—Jacelyn Ram
(74) Attorney, Agent, or Firm—Thomas, Kaydon, Horstemeyer & Risley, LLP

(57) ABSTRACT

A self-contained surgical warming device 10 includes a flexible outer bag having a heat generating compound 40 which becomes activated when exposed to air. In use, a surgical assistant or nurse wraps a surgical instrument such as an endoscope 18 in the warming device. The warming device then transfers enough heat to the endoscope to raise the temperature of the endoscope to approximately that of body temperature, thereby preventing the condensation of water vapor on a camera lens in an endoscopic instrument. The surgical instrument warming device may be used on endoscopes or any other type of surgical instrument that requires warming to approximately body temperature prior to contact with human tissue.

5 Claims, 3 Drawing Sheets

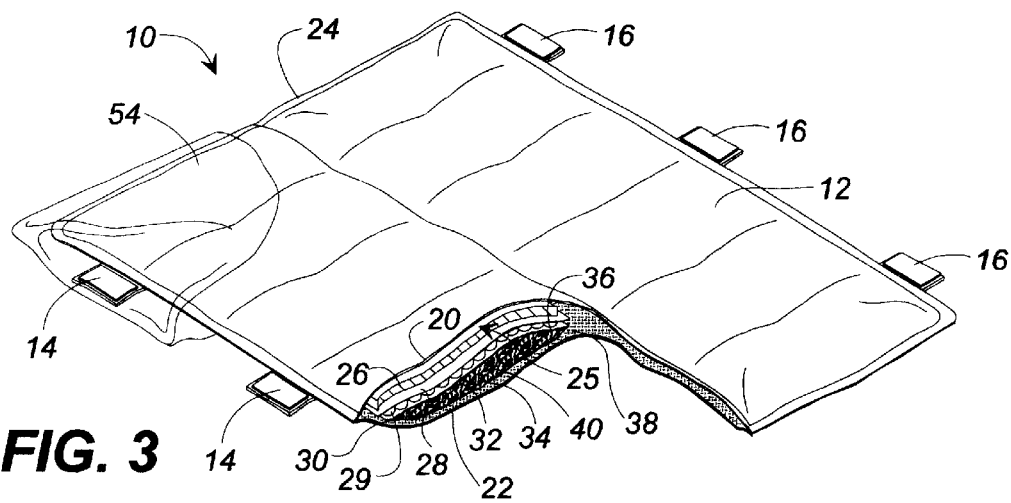
FIG. 3
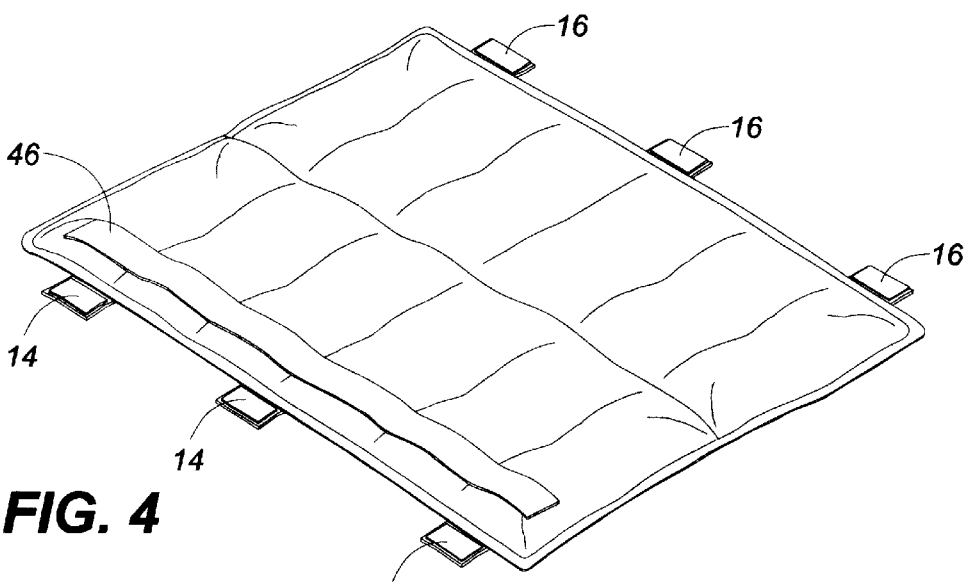
FIG. 4
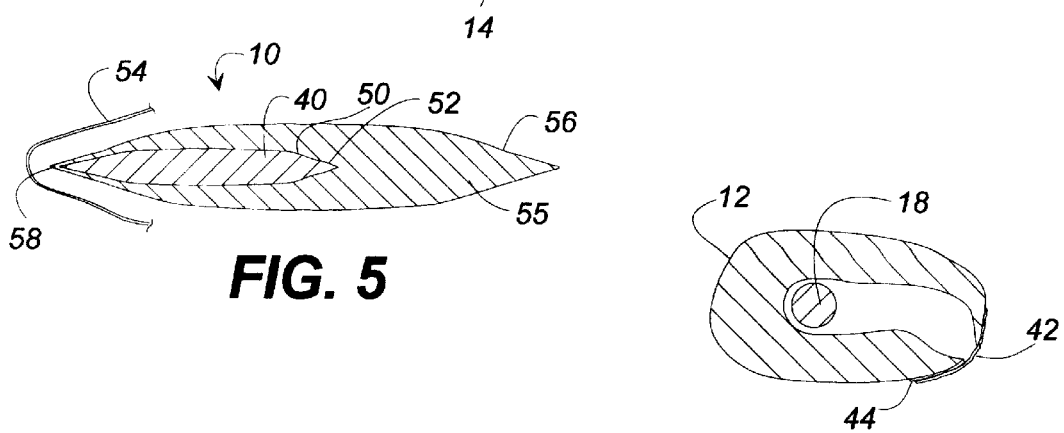
FIG. 5
FIG. 6

SURGICAL INSTRUMENT WARMING DEVICE

CROSS REFERENCE

This application claims the benefit of U.S. Provisional Application Ser. No. 60/094,371, filed Jul. 27, 1998.

FIELD OF THE INVENTION

The present invention relates generally to the field of surgical instrumentation and consumable items associated therewith. More specifically, the present invention relates to a disposable device for warming surgical instruments.

BACKGROUND OF THE INVENTION

Surgical use of laproscopic or endoscopic instruments has become more frequent in recent years. Once used almost exclusively for orthopedic procedures, the use of endoscopic devices has expanded to corrective procedures associated with the shoulder and spine. Additionally, endoscopic devices enjoy an expanded use in imaging the interior viscera including interior surfaces of the stomach, small intestines, and colon. The use of endoscopic devices has been expanded to heart surgery as well and for the removal of gall bladders. Each application dictates a specific shape of an endoscope.

In the operating room environment, a first sterile back field is arranged and configured to accept and store surgical instrumentation, where the surgical assistant works to organize, prepare and manage orthoscopic equipment before, during and after surgery. After preparation for surgery, the patient lies in a second sterile back field immediately surrounding the patient. During endoscopic surgery, the surgeon or his assistant may place the endoscope in the first sterile back field adjacent to other surgical instruments before and between uses.

One problem common to the use of endoscopic devices relates to the temperature difference between the operating room air and that of the human tissue. For example, the operating room temperature is approximately 14° C. to approximately 18° C., which is considerably lower than the 37° C. body temperature of a patient. If a surgeon inserts an endoscope at operating room temperature into an incision at body temperature, the moisture in the incision condenses on the endoscope lens as a result of the temperature difference in the moist environment Lens condensation impedes image input to the camera and further causes a distorted or blurry video signal, which impedes a surgeon's ability to view a patient's anatomy in the operative anatomical area.

Surgeons have developed techniques to prevent an endoscopic lens from fogging due to temperature differences between the scope and patient tissue. A most common solution eliminates the temperature difference between the scope and tissue by warming the scope prior to insertion in patient tissue so that there will be no condensation on the scope. Several warming techniques are commonly known.

One warming technique utilizes an electric warming pad to heat the scope. Although effective at raising the endoscope temperature, problems arise out of the requirement for a power source for warming pads. The endoscopic surgical environment typically abounds with cable feeds from fiber optic equipment, video feeds and power lines. Thus, an additional cable for a warming pad is undesirable in that it adds to the operating room clutter. Furthermore, if operating room personnel trip over the cord, the endoscope may fall from its table to the floor and become damaged. Endoscopes are extremely expensive and such falling risks are undesirable.

Another solution to the problem of condensation forming on the lens of a scope entails immersing the endoscope in a sterile saline bath maintained at least at body temperature. Disadvantages associated with the saline immersion warming method include possible spillage of the saline solution, the cumbersome nature of an open liquid container in the operating room environment and the corrosive effect of the saline solution on the scope With the forgoing disadvantages of the prior art in minds it is an object of the present invention to provide a warming device which safely warms a surgical instrument without the need for an energy source separate from the warming device.

It is another object of the present invention to provide a warming blanket which protects and encapsulates a surgical instrument such as an endoscope, in event that the endoscope falls from a table to a floor in the operating room environment.

It is another object of the present invention to provide a surgical warming device which is capable of withstanding gamma radiation for sterilization purposes.

It is another object of the present invention to provide a surgical instrument warming device which surrounds and protects the instrument sterility.

It is another object of the present invention to provide a surgical instrument warming device which maintains heat between uses on a single patient.

It is another object of the present invention to provide a surgical instrument warming device which is completely portable.

It is another object of the present invention to provide a surgical instrument warming device which assumes its own flat surface for facilitating stability of the surgical instrument on a surface in the sterile field.

It is another object of the present invention to provide a surgical instrument warming device which is opened in the secondary sterile field to maintain sterility of the warming device.

It is another object of the present invention to provide a surgical instrument warming device which has an upper heat limit to prevent tissue damage.

It is another object of the present invention to provide a surgical instrument warming device which absorbs fluids from the surgical instrument after use on a patient.

It is another object of the present invention to provide a surgical instrument warming device which is manufactured, inserted within a sealed bag, then sterilized.

Other objects, features and advantages of the present invention will become apparent upon reading the following specification, when taken in conjunction with the accompanying drawings.

SUMMARY OF THE INVENTION

Generally speaking, the present invention relates to an apparatus for warming a surgical instrument before and between uses on a single patient. More specifically, the present invention relates to a self-contained, disposable, single-use apparatus for warming and protecting a surgical instrument in a sterile back field.

The self-contained apparatus may essentially comprise a flexible outer bag enclosing heat generating compounds which become activated when mixed with one another and when exposed to air. A surgical assistant squeezes and/or shakes the outer bag to mix the interior components to initiate the generation of heat and wraps a surgical instrument, such as an endoscope, in the warmer, by folding the warmer about the instrument. The warming device then transfers enough heat to the endoscope necessary to raise the endoscope temperature to approximately body temperature, thereby preventing condensation of water vapor on a camera lens (fogging), which often occurs when a relatively cold endoscope contacts warm body tissue. The surgical warming device wraps around the instrument, takes no longer than approximately 15 minutes to heat the surgical instrument to approximately body temperature, is completely self-contained, and is easily discarded after a single use (a single use is considered to be one surgical procedure on a single patient).

In one embodiment of the present invention, the surgical instrument warming apparatus includes a sterile, flexible outer bag which contains the heat-generating materials and has external surfaces arranged and configured to fold about and to at least partially enclose a surgical instrument, wherein the outer bag includes an inner cavity and perforations through the outer bag for allowing air to pass into the outer bag inner cavity. Alternatively, the bag fabric may be air permeable for allowing air to pass to the outer bag inner cavity. The apparatus may also include an inner bag disposed within the cavity of the outer bag, wherein the inner bag includes perforations to pass air from the inner cavity of the outer bag to an inside cavity of the inner bag. The inner and outer bags may be formed from any material, and most preferably a non-woven web.

The inner bag includes in its inner cavity a heat generating composition which activates when exposed to air. In a preferred embodiment, the heat generating compound includes iron powder, water active carbon and a salt. When the compound is exposed to air, it conducts an exothermic reaction to produce heat. Relative weight percentages of various constituents of the heat generating compound may be manipulated to adjust the maximum apparatus temperature, time to achieving the maximum apparatus temperature, and duration of the warming effect of the apparatus. In a preferred embodiment, the maximum temperature of the apparatus is approximately equal to that of body temperature, which is approximately 37° C. Additionally, the time to achieving maximum apparatus temperature is formulated to allow the surgical instrument to achieve body temperature approximately 15 minutes after being placed in the warming device.

The present invention may also include a mechanism for releasably maintaining the bag in a folded enclosing position around the surgical instrument before and between uses of the surgical instrument. In one embodiment, the fastening mechanism may include at least one pair of hook and loop fasteners. For example, a first fastener in the pair extends from one peripheral edge of the warming device and a second fastener adapted to mate with the first fastener extends from an opposite peripheral edge of the warming device wherein the pair of fasteners is arranged and configured to attach and interlock after the apparatus encloses the surgical instrument. Alternatively, the warming apparatus may include hook and loop fasteners disposed on surfaces of the apparatus, near peripheral edges thereof, wherein the fastener pairs contact one another after receiving the surgical instrument within a pocket formed by a fold in the bag. In another embodiment, the fastening means may include at least one strip of longitudinal material extending from a periphery of the apparatus. The strip may include adhesive on one side thereof of for allowing the strip to be fastened to another portion of the apparatus when the apparatus is folded for enclosing the surgical instrument. Alternatively, the warming apparatus may include adhesive portions disposed on a surface of the apparatus, near peripheral edges thereof.

The invention may also include an air tight package enclosing the entire apparatus and capable of withstanding gamma ray radiation sterilization. In this embodiment, the package maintains sterility of the apparatus until opened in a sterile back field within a surgical environment.

In a preferred embodiment, the outer bag of the warming device is substantially flat, and includes one surface that usually faces upwardly before the bag is folded to form the pocket for the instrument and when folded forms the surfaces of the pocket of the apparatus end which is adapted to contact the surgical instrument, and a bottom surface opposite the upper surface that usually faces downwardly before the bag is folded. The outer bag includes an inner cavity which encloses an air permeable inner bag. The inner bag encloses a heat generating compound which generates heat when exposed to air. The outer bag perforations are disposed in the outer bag upper surface for allowing air to permeate the inner cavity and inner bag and for directing heat transfer to the surgical instrument.

The surgical instrument warming device may also include a sheet of flexible polymeric foam material disposed within the inner cavity of the outer bag and adjacent to one side of the inner bag, with the inner bag disposed, wherein the sheet of polymeric foam regulates heat transfer from the heat generating compound to the surgical instrument, and provides padding for protection of the surgical instrument in the event of a fall from a supporting surface. The warming device may also include a sheet of polymer disposed adjacent to the polymeric foam, wherein the polymer sheet includes capsules of air stored therein for adding additional padding for protection of the surgical instrument during a fall from a supporting surface.

The present invention also relates to a method for warming and protecting a surgical instrument in a sterile back field comprising the steps of removing a sterile, self-contained heating apparatus from a protective package to initiate an air-activated heat generating composition within the apparatus, placing the surgical instrument in the heating apparatus for allowing heat to transfer from the apparatus to the instrument, and maintaining the surgical instrument at approximately body temperature before or between uses of the instrument on a single patient.

The method may also include the step of releasably fastening the apparatus around the surgical instrument prior to or between uses to prevent the surgical instrument from dismounting from the apparatus. Additionally, the step of releasably fastening the apparatus around the surgical instrument includes the step of utilizing interlocking hook and loop fasteners at peripheral edges of the apparatus to one another to shape the apparatus into a wrapped configuration. The method may also include the step of providing strips of material having adhesive on at least one side thereof for fastening peripheral edges of the apparatus to one another to shape the apparatus into a wrapped configuration around the surgical instrument.

Other objects, features and advantages of the present invention will become apparent upon reading the following specification, when taken in conjunction with the accompanying drawings.

BRIEF DESCRIPTION OF THE DRAWINGS

The accompanying drawings incorporated in and forming a part of the specification illustrate several aspects of the present invention, and together with the description serve to explain the principles of the invention. The components in the drawings are not necessarily to scales emphasis instead being placed upon clearly illustrating principles of the present invention. In the drawings appended hereto, like numerals illustrate like parts throughout the several views.

FIG. 3 illustrates a perspective view of the surgical instrument in a open position, taken in a partial cross-section, illustrating various contents in an inner cavity of the warming device.

FIG. 4 illustrates a perspective view of an alternative embodiment of the inventive surgical instrument warming device.

FIG. 5 illustrates a sectional view of an alternative embodiment of a surgical instrument warming device in accordance with the present invention.

FIG. 6 illustrates a sectional view of yet another embodiment of a surgical instrument warming device in accordance with the present invention.

Figure 1:
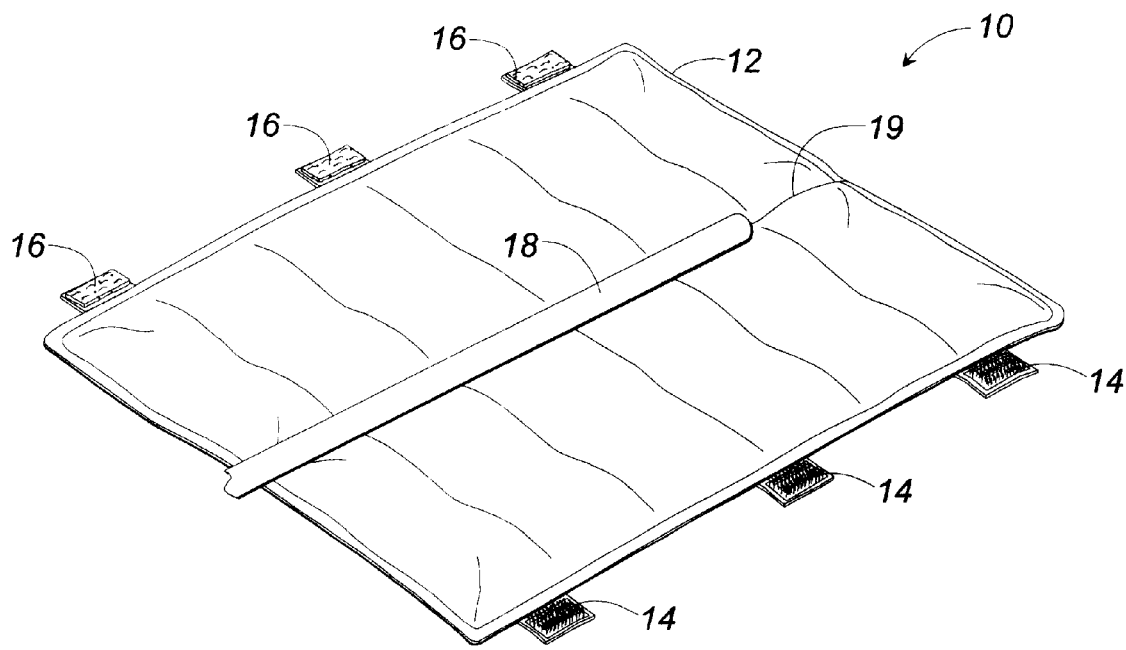
FIG. 1 illustrates a perspective view of the surgical instrument warming device disposed in an open position, with a schematically illustrated surgical instrument disposed on a top portion thereof.

Reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims.

DETAILED DESCRIPTION OF THE PREFERRED EMBODIMENTS

Figure 2:
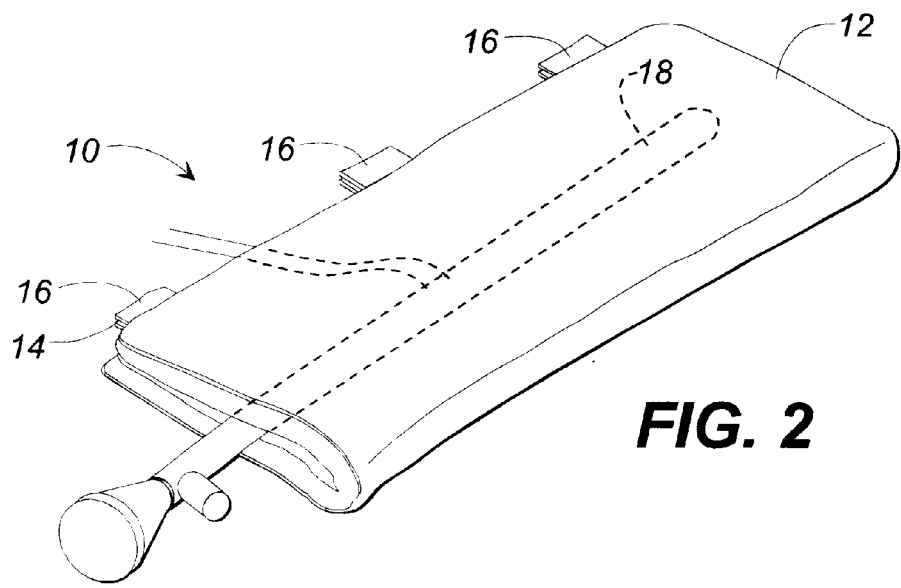
FIG. 2 illustrates a perspective view of the surgical instrument warming device disposed in an closed position, wrapped around a schematically illustrated surgical instrument.
Figure 8:
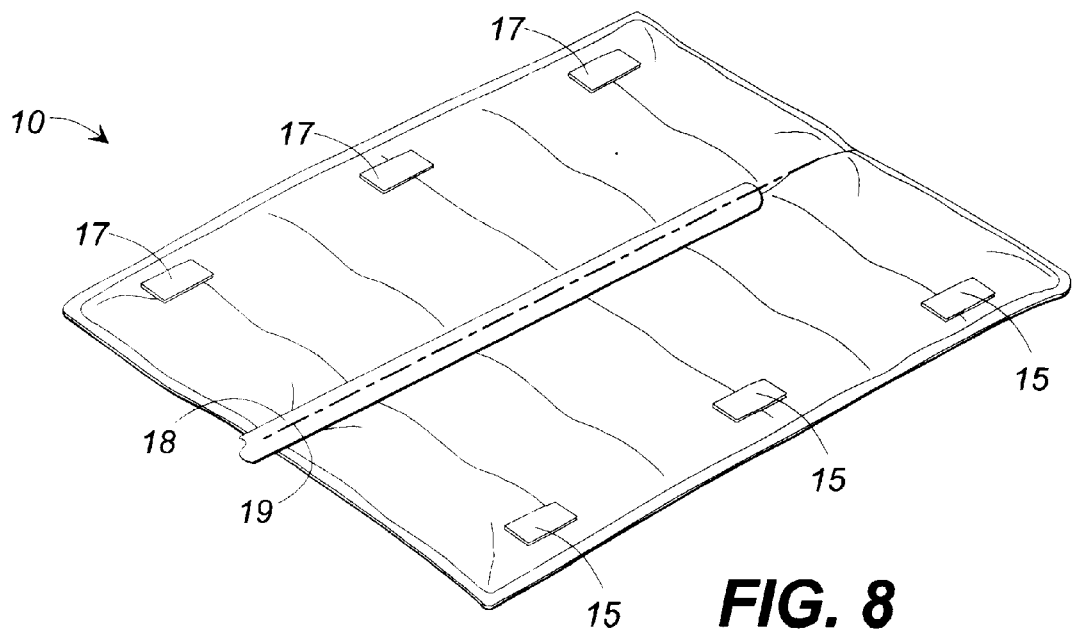
FIG. 8 illustrates a view of yet another embodiment of the surgical instrument warming device in accordance with the present invention.

Referring now to the drawings in detail, FIG. 1 illustrates a surgical instrument warming device 10 shown in a flat, open position with a surgical instrument 18 such as an endoscope placed along a fold-line 19. When in an open position, the warming device 10 is generally flat and it comprises an essentially solid rectangular shape. However, as discussed in greater detail below, the warming device may assume generally any shape necessary to envelope, wrap around, or otherwise cover a surgical instrument for the purposes of warming and protecting the surgical instrument. Warming device 10 includes a number of fastening devices which are adapted to fasten the warming device around a surgical instrument. For example, hook and loop pairs 14 and 16 may extend laterally outward from a peripheral edge of the warming instrument. As is illustrated in FIG. 2, the warming device 10 wraps around surgical instrument 18, shown in dashed lines, and hook and loop fastening pairs 16 and 14 close together to releasably fasten the warming device in a folded position. Alternatively, as shown in FIGS. 8, the warming device 10 may include hook and loop devices 15 and 17 disposed on a peripheral inside surface of the warming device 10. When the surgical technician or surgeon folds the warming device 10 around the surgical instrument 18, hook and loop device pairs 15 and 17 engage one another to releasably enclose the surgical instrument 18.

FIG. 3 illustrates a perspective view of the warming device in partial section to illustrate inside contents thereof. Warming device 10 includes an outer bag 12 preferably comprised of a non-woven fabric formed from polymer and/or paper fibers for increasing strength and absorbency of the material. The warming device 10 also includes a border 24 which may comprise a glued seam of upper and lower sheets 20 and 22 of the outer bag 12. If necessary, the inside cavity 25 of outer bag 12 may include a polymeric foam sheet 26 for additional padding and for insulating an outer side of the warming device 10, such that the opposite side of the warming device 10, which faces the surgical instrument 18, transfers a maximum amount of heat to the instrument. Additionally, the padding protects the surgical instrument if it falls from a table to the floor. An underside of polymeric foam sheet 26 may include an air cushion material 28 disposed thereunder, which is comprised of a polymer sheet having a plurality of air-filled capsules 29 incorporated integrally therein.

Disposed beneath the air cushion material 28 is an inner bag 30 having upper and lower air permeable inner bag layers 32 and 34, respectively. Inner bag 30 includes perforations 36 disposed on inner bag layers 32 and 34 for allowing air to contact heating agent 40. Additionally, one or both sides of the outer bag 12 may include perforations 38 for allowing air to penetrate the outer bag and inner bag to contact the heating agent 40. The heating agent 40 may be a heat generating composition comprised of iron powder as a main ingredient and, incorporated therein, water, a water-retaining material (charcoal vermiculite or the like), an oxidation promoter such as activated carbon, and salt. More particularly, the agent may comprise about 50–65% by weight of iron powder, 18–22% by weight of water, 9–11% by weight of a water-retaining agent, 3.5–4.5% by weight of an activated carbon, and about 4.5–6% by weight of salt. During manufacturing, the entire surgical instrument warming device 10 is inserted into an air impermeable packaging bag 54, whereupon hermetic sealing of the periphery of the packaging bag is conducted. After removal of the air impermeable packaging 54 from about the warming device 10, a surgical technician squeezes the bag to mix the heat generating compound and oxidation of the iron begins in an exothermic reaction which generates heat. In the particular embodiment, a surgical warming device temperature of 37° Celsius is desired so that the surgical instrument may be warmed to that of body temperature.

Although the surgical instrument warming device may have any size, it is generally preferred so as to have an area sufficient to cover any surgical instrument almost completely. For example, most endoscopic instruments are approximately 16 inches in length. It is therefore desirable to make the pad approximately 16 inches in length so that the pad may be folded over and form a pocket about the entire length of the endoscopic instrument. It is preferred and required that the outer bag layer be biocompatible. Examples of materials which may be used to fabricate the outer bag include polyurethane, polypropylene, polyethylene, plastic, rubber materials and non-woven fabric as discussed above. Air permeability of the bag is required. Micropores in the above-referenced sheets or films may be utilized to accomplish air permeability.

In use, sterile or non-sterile personnel may remove the surgical instrument warming device 10 from its air impermeable packaging bag 54 and drop the onto a sterile back field next to other instruments. A sterile surgical technician may then manipulate the surgical instrument warming device to begin the exothermic reaction by massaging the warming device 10 to mix the various components of the heat generating agent therein. The surgical technician may then lay the surgical instrument such as an endoscope along a fold line 19, as illustrated in FIG. 1, and fold the warming device 10 over the surgical instrument 18 to enclose the surgical instrument 18 within the warming device. The surgical technician may then fasten hook and loop fasteners 14 and 16 together and ready the instrument for use. In a preferred embodiment, the warming device takes no longer than 15 minutes to warm the surgical instrument to body temperature or within 5° Celsius thereof. Additionally, in a preferred embodiment, the pad may provide heat to keep the surgical instrument warm for up to 2 hours. After the surgeon's technician readies the patient for the operation, the surgeon may then remove the surgical instrument 18 from the warming device by opening the hook and loop fasteners 14 and 16 or 15 and 17 to expose the instrument, couple a fiber optic light and cable to the instrument and couple a video feed for a camera to the endoscope. If the endoscope is withdrawn from the patient periodically, the warming device 10 may accept the endoscope once again and the outer periphery of the surgical instrument near the fasteners 14 and 16 may allow for the cables still connected to the instrument to project out of the lateral portion thereof.

FIG. 4 illustrates an alternative embodiment of the warming device 10 which includes a longitudinal adhesive strip 46 disposed along a periphery of the pad. In this embodiment, the surgical technician may simply fold the bag over the instrument so that adhesive strip 46 adheres to an opposite side of the warming device 10 to enclose the endoscope or other surgical instrument therein.

FIG. 5 illustrates an alternative embodiment of the present invention wherein an outer bag 56 encloses a packaging portion 55 and an inner bag 50 which encloses the heat agent 40 in an air-tight manner. When squeezed or crushed, the preformed outlet 52 may burst open and expose the contents to air to generate an exothermic reaction as described above. Packaging bag 54 encloses the heat heating agent 40 after preformed outlet 52 bursts open. This embodiment is useful when air impermeable packaging bag 54 is removed for the purpose of placing the warming device 10 into the sterile field. When the warming device 10 is needed to generate heat, sterile personnel may squeeze the package to burst the preformed outlet 52. Thus, an unlimited amount of time may pass between the removal of packaging bag 54 and the rupture of preformed outlet 52.

FIG. 6 illustrates another embodiment of the present invention in which the outer bag 12 encloses a surgical instrument 18 such as an endoscope, wherein the outer bag 12 includes an adhesive strip 42 projecting from an outer periphery thereof to contact an adhesive 44 on an opposite side of the bag 12. The adhesive strips may be easily removed to expose the instrument and reattached at a later time for further warming of an instrument during a surgical procedure.

Figure 7:
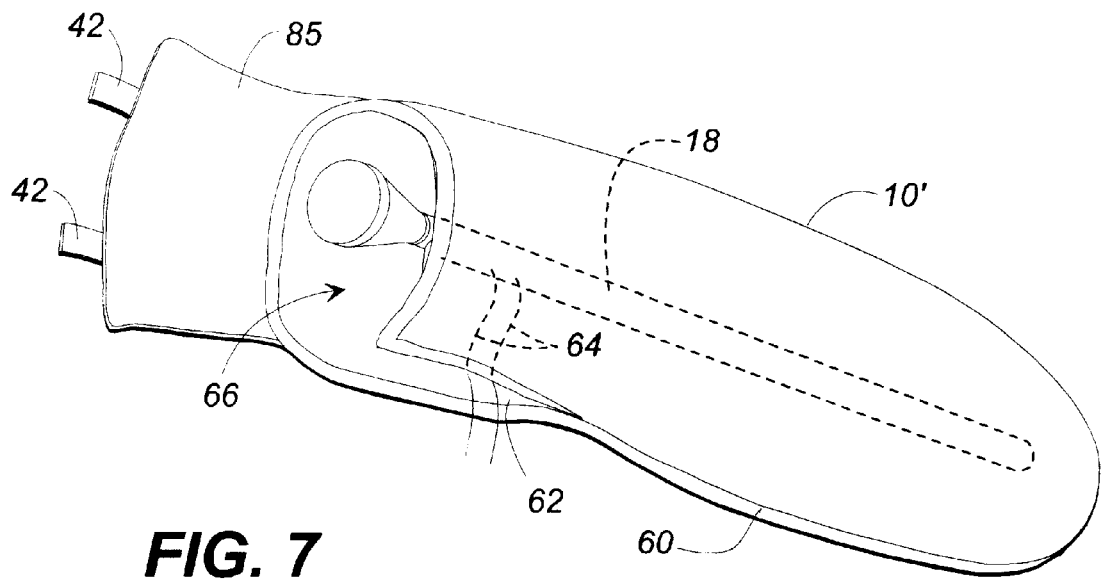
FIG. 7 illustrates a perspective view of yet another embodiment of the surgical instrument warming device in accordance with the present invention.

Finally, FIG. 7 illustrates yet another alternative embodiment of the present invention which includes a tubular or envelope-like embodiment which houses the surgical instrument 18 therein. This particular embodiment also includes a slit 62 which allows a peripheral cable 64 to project out of the envelope. Thus, the surgical instrument 18 may easily be inserted through aperture 66 in the envelope-like warming device 10'. The warming device may include a seam 60 which is a continuation of the slit 62. In this embodiment, the warming device may have the same construction as that disclosed in FIG. 3, but comprises a seam 60 which represents a permanent fastening device to keep the warming device 10' in a folded position Finally, this embodiment may include a flap cover 85 which folds over and closes aperture 66. Flap Cover 85 may also include adhesive strips 42 for keeping the flap closed.

The foregoing description has been presented for purposes of illustration and description. It is not intended to be exhaustive or to limit the invention to the precise forms disclosed. Obvious modifications or variations are possible in light of the above teachings. The embodiment or embodiments discussed were chosen and described to provide the best illustration of the principles of the invention and its practical application to thereby enable one of ordinary skill in the art to utilize the invention in various embodiments and with various modifications as are suited to the particular use contemplated. For example, the surgical warming instrument may be of nearly any shape which is necessary to accomplish the purposes of the present invention as described above. Additionally, although specific chemicals have been enumerated for use in the heat generating composition, any other type of chemical which may generate heat for the purpose of warming the surgical instrument by using an exothermic reaction would also be suitable for use in the present invention.

All such modifications and variations are within the scope of the invention as determined by the appended claims when interpreted in accordance with the breadth to which they are fairly and legally entitled.

What is claimed is:

1. A method for self warming and protecting a surgical instrument in a sterile back field, the method comprising the steps of:

removing a sterile, self-contained heating apparatus from a protective package;

initiating an air-activated heat generating composition within the heating apparatus; and wrapping the surgical instrument in the heating apparatus for allowing heat to transfer from the apparatus to the instrument.

2. The method of claim 1 comprising the further step of:

heating and maintaining the surgical instrument at approximately body temperature before and between uses on a single patient.

3. The method of claim 1 comprising the further step of:

releasably fastening the apparatus around the surgical instrument prior to and after use to prevent the surgical instrument from dismounting from the apparatus.

4. The method of claim 3, wherein the step of releasably fastening the apparatus around the surgical instrument includes the step of utilizing interlocking hook and loop fasteners at peripheral edges of the apparatus to one another to shape the apparatus into a wrapped configuration.

5. The method of claim 3, wherein the step of releasably fastening the apparatus around the surgical instrument includes the step of fastening strips of material having adhesive on at least one side thereof for fastening peripheral edges of the apparatus to one another to shape the apparatus into a wrapped configuration.

* * * * *